(12) United States Patent
Qin et al.

(10) Patent No.: US 12,306,279 B2
(45) Date of Patent: May 20, 2025

(54) QUANTITATIVE MAPPING OF MRI RELAXATION PARAMETERS

(71) Applicant: THE JOHNS HOPKINS UNIVERSITY, Baltimore, MD (US)

(72) Inventors: Qin Qin, Ellicott City, MD (US); Dan Zhu, Baltimore, MD (US); Ruoxun Zi, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 182 days.

(21) Appl. No.: 17/792,614

(22) PCT Filed: Jan. 13, 2021

(86) PCT No.: PCT/US2021/013301
§ 371 (c)(1),
(2) Date: Jul. 13, 2022

(87) PCT Pub. No.: WO2021/146335
PCT Pub. Date: Jul. 22, 2021

(65) Prior Publication Data
US 2023/0044359 A1 Feb. 9, 2023

Related U.S. Application Data

(60) Provisional application No. 62/960,305, filed on Jan. 13, 2020.

(51) Int. Cl.
*G01R 33/56* (2006.01)
*A61B 5/00* (2006.01)
*A61B 5/055* (2006.01)

(52) U.S. Cl.
CPC ........ *G01R 33/5608* (2013.01); *A61B 5/0042* (2013.01); *A61B 5/055* (2013.01)

(58) Field of Classification Search
CPC .... G01R 33/5608; A61B 5/055; A61B 5/0042
See application file for complete search history.

(56) References Cited

U.S. PATENT DOCUMENTS

| | | | | |
|---|---|---|---|---|
| 6,486,667 B1 * | 11/2002 | Wu | ...................... | G01R 33/563 324/309 |
| 8,334,694 B2 * | 12/2012 | Tan | ...................... | G01R 33/243 324/309 |
| 2014/0126796 A1 | 5/2014 | Chesneau et al. | | |
| 2014/0292330 A1 | 10/2014 | Gulani et al. | | |
| 2015/0310639 A1 | 10/2015 | Berkin et al. | | |
| 2018/0310869 A1 * | 11/2018 | Yablonskiy | ........ | A61B 5/14542 |

OTHER PUBLICATIONS

Salminen, Lauren E et al. "Reducing CSF Partial Volume Effects to Enhance Diffusion Tensor Imaging Metrics of Brain Microstructure." Technology and innovation vol. 18, 1 (2016): 5-20. doi:10. 21300/18.1.2016.5 (Year: 2016).*

Felix Lugauer et al., Accelerating multi-echo wafer-fat mri with a joint locally low-rank and spatial sparsity-promoting reconstruction, Magn reson mater PHY, 2017, 30: 189-202.

* cited by examiner

*Primary Examiner* — Gregory H Curran

(57) ABSTRACT

Magnetic resonance imaging according to the present invention includes T1, T2, or diffusion mapping with improved image resolution. The improved image resolution is achieved by leveraging the delay in the image acquisition to remove the partial volume effect of fluid in and around the tissue being imaged.

12 Claims, 4 Drawing Sheets

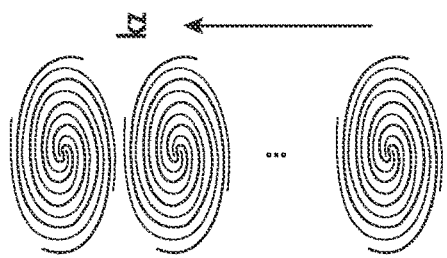
FIG. 1B
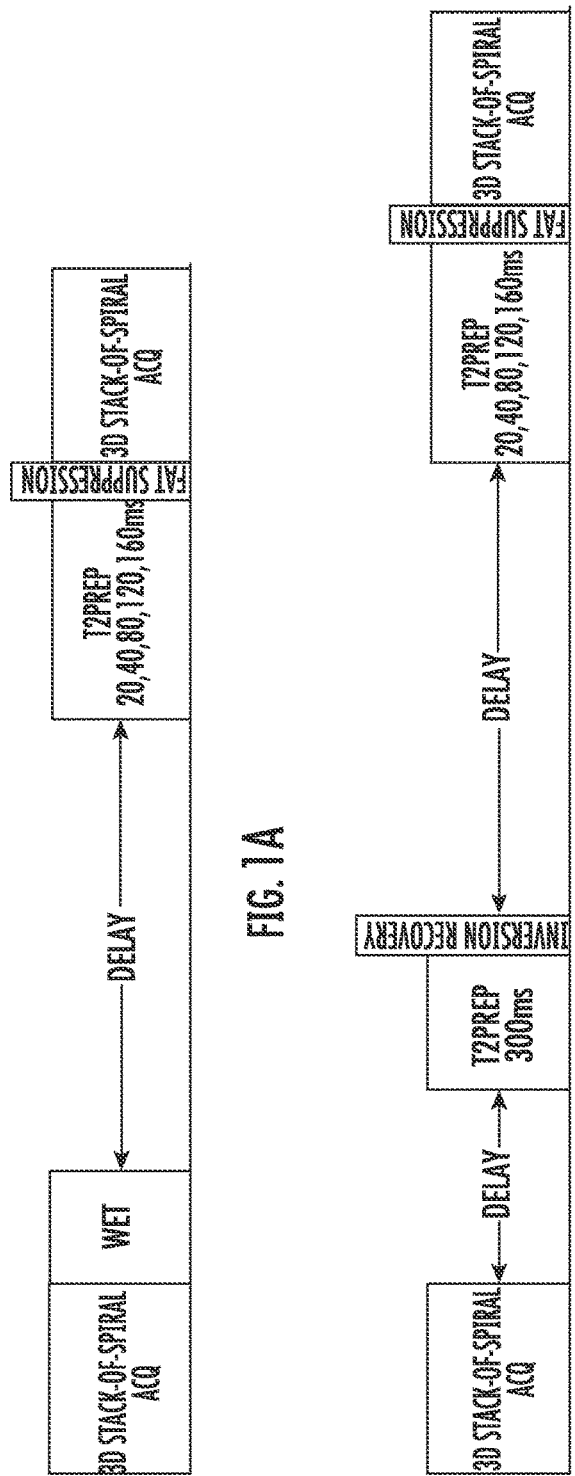
FIG. 1A
FIG. 1C

US 12,306,279 B2

QUANTITATIVE MAPPING OF MRI RELAXATION PARAMETERS

CROSS-REFERENCE TO RELATED APPLICATIONS

This application is a 35 U.S.C. § 371 U.S. national entry of International Application PCT/US2021/013301, having an international filing date of Jan. 13, 2021, which claims the benefit of U.S. Provisional Application No. 62/960,305, filed Jan. 13, 2020, the content of each of the aforementioned applications is herein incorporated by reference in their entirety.

FIELD OF THE INVENTION

The present invention relates generally to medical imaging. More particularly, the present invention relates to a system and method for quantitative mapping of MRI relaxation parameters with minimized partial volume effect.

BACKGROUND OF THE INVENTION

Conventional T1, T2, or diffusion mapping procedures include acquisition of the same k-space datasets at different contrast weighting, followed by individual image reconstruction and subsequent voxel-by-voxel model fitting. The long scan time associated with reliable parametric dimension sampling is an obstacle for practical utility and requires high undersampling at levels which are beyond capabilities of conventional reconstruction techniques such as parallel imaging. The resultant images can also include bright spots caused by the partial volume effect of fluid in and around the tissue being imaged. These bright spots can clutter the visual and make the resultant image more difficult to read.

It would therefore be advantageous to provide a system and method for quantitative mapping of MRI relaxation parameters with minimized partial volume effect.

SUMMARY OF THE INVENTION

The foregoing needs are met by the present invention which provides a method for obtaining a magnetic resonance image or spectrum of a subject, including an inversion module to null fluid signal and minimize the partial volume effect.

In accordance with an aspect of the present invention, the method includes applying the inversion module to a T1 pulse sequence, a T2 pulse sequence, and/or a diffusion pulse sequence. The method includes applying a pulse sequence for 3D mapping.

In accordance with another aspect of the present invention, a method for obtaining a magnetic resonance image or spectrum of a subject, includes applying a prepared stack-of-spiral gradient-echo (GRE) pulse sequence for 3D mapping. The method includes applying a model-based reconstruction method with spatial sparsity regularization for mapping. The method also includes an inversion module to minimize the partial volume effect.

In accordance with still another an aspect of the present invention, the method includes applying the prepared stack-of-spiral gradient-echo pulse sequence with CSF nulling. The method includes applying the prepared stack-of-spiral gradient-echo pulse sequence without CSF nulling. The method also includes applying a T1, T2, or T1 and T2 prepared stack-of-spiral gradient-echo (GRE) pulse sequence for 3D T1 mapping. The prepared stack-of-spiral GRE pulse sequence can also be applied for 3D diffusion mapping.

BRIEF DESCRIPTION OF THE DRAWINGS

FIG. 1A illustrates a schematic diagram of a T2 prepared 3D stack-of-spiral sequence without CSF nulling.

FIG. 1B illustrates a view of a 3D stack-of-spiral trajectory, with TFE encoding applied on kz dimension and variable density spiral trajectory (Accel=2) applied in plane.

FIG. 1C illustrates a schematic diagram of a T2 prepared 3D stack-of-spiral sequence with CSF nulling.

DETAILED DESCRIPTION

Figures 2A, 2B:
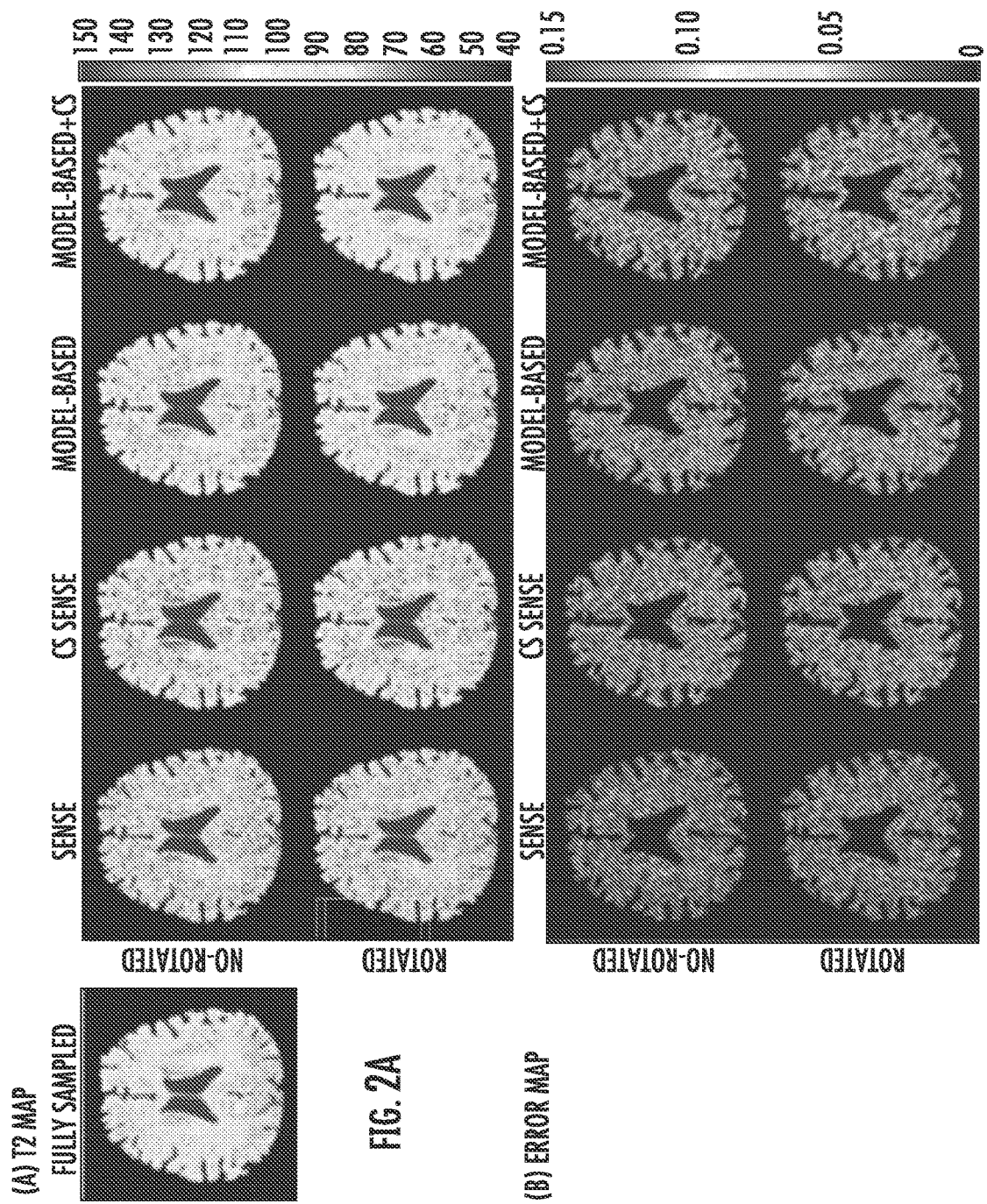
FIGS. 2A and 2B illustrate image views of T2 maps and corresponding normalized error maps estimated by different reconstruction methods.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system and method for magnetic resonance imaging including T1 and/or T2, and/or diffusion mapping with improved image resolution. The improved image resolution is achieved by leveraging the delay in the image acquisition to remove the partial volume effect of fluid in and around the tissue being imaged.

Quantitative relaxometry is a desired MRI tool for longitudinal or cross-sectional characterization of lesion structures. Conventional $T_2$ mapping methods generate and reconstruct $T_2$ weighted images frame-by-frame followed by voxel-wise fitting. The associated long acquisition time hinders its practical utility, especially for applications that require 3D high spatial resolution and broad volume coverage.

Various rapid imaging techniques have been adapted to $T_2$ mapping experiments. Parallel imaging exploits the data redundancy generated by multiple receiver coils to recover missing k-space samples. With the development of compressed sensing (CS), several constrained reconstruction methods have been developed for acceleration and applied to parameter mapping. One study proposed iterative reconstruction using a total variation (TV) constraint on radial acquisition; another applied sparsifying transform on images acquired with incoherent sampling for acceleration. In addition to the undersampling of spatial characteristics, redundancy in the temporal or parametric dimensions of image series has been explored as well. Some methods combined the aforementioned constraints. Another promising strategy for fast parameter mapping is model-based reconstruction, which incorporated the underlying signal model as prior knowledge in an iterative reconstruction to estimate parameter maps directly from k-space data. Advanced reconstruction imposing subspace constraints has also been demonstrated for parameter mapping.

A majority of these studies applied 2D multi-slice acquisition with Cartesian trajectories, which achieved up to 5-fold acceleration. 3D acquisition typically uses the smaller slice thickness without gaps and even isotropic resolution, which allows visualization of small lesions in any reformatted orientation. 3D radial trajectory has been adopted for $T_1$ and/or $T_2$ estimation with undersampling. Spiral trajectory offers the great advantages of high acquisition efficiency and accelerated reconstruction, as well as robustness to motion artifacts. 3D $T_2$ mapping has been performed using pulse sequences based on gradient echo (GRE) steady state conditions, multi-echo fast spin echo (FSE), or $T_2$ magnetization preparation followed by GRE or FSE.

During the last decade or so, brain $T_2$ mapping has largely been applied with advanced 2D acquisitions and few with 3D methods. In the clinical setting, multi-parametric MRI would be straightforward for corregistration when different magnetization preparation modules are appended with the same acquisition readout. The present invention is directed to a directed to a system and method for magnetic resonance imaging including T1 and/or T2, and/or diffusion mapping with improved image resolution. The improved image resolution is achieved by leveraging the delay in the image acquisition to remove the partial volume effect of fluid in and around the tissue being imaged. In particular, an exemplary implementation shows a $T_2$-prepared GRE sequence combined with 3D stack-of-spiral acquisition for $T_2$ mapping with whole-brain coverage and high spatial resolution. Different fitting models, k-space sampling strategies, and reconstruction techniques were evaluated in both numerical simulation and brain scans for optimum performance. Suppression of cerebrospinal fluid (CSF) signal to reduce its partial volume effect was also tested for brain $T_2$ quantification.

The present invention includes a method for obtaining a magnetic resonance image or spectrum of a subject using an inversion module to null fluid signal and minimize the partial volume effect. This methodology can be applied to T1, T2, or diffusion mapping. Improved image resolution is achieved by leveraging the delay in the image acquisition to remove the partial volume effect of fluid in and around the tissue being imaged. In addition, use of the inversion module can be paired with any number of pulse sequences known to or conceivable to one of skill in the art. The pulse sequence can be chosen based on whether T1, T2, or diffusion mapping is being applied, as well as any other factors known to or conceivable to one of skill in the art. Herein, a T2 prepared stack-of-spiral gradient-echo (GRE) pulse sequence is used to further illustrate the invention. This pulse sequence and its particular application to use with a T2 imaging methodology are include herein, simply by way of example, and are not meant to be considered limiting.

On MRI, lesions often have higher T1 and T2 or diffusion, which can be difficult to identify due to tissue partial volume effect of fluid. Normal fluid can be nulled to remove its partial volume effect by using an inversion based module before the acquisition module. Quantitative mapping of MRI relaxation parameters such as T1, T2, and diffusion are important for clinical characterization of lesion structure and is desired for longitudinal or cross-sectional comparison. Therefore, T1, T2, or diffusion mapping combined with a fluid-nulling method to minimize partial volume effect could significantly improve the clinical utility of the quantification method. Instead of suppressing the fluid signal using modified sequences, other T1 and T2 or diffusion quantification methods either assume no fluid partial volume effect or quantify the data using two compartment models. Fitting data with 2-compartment models require very high SNR and is not feasible for clinical MRI. The work related to the present invention was done to determine the process and In an exemplary implementation of the present invention, a T2 prepared stack-of-spiral gradient-echo (GRE) pulse sequence is applied with or without CSF nulling for 3D T2 mapping of the brain. A model-based reconstruction method with spatial sparsity regularization for T2 estimation is applied. Alternately or in conjunction a T1 sequence can also be applied and a model-based reconstruction method used to minimize the partial volume effect.

FIG. 1A illustrates a schematic diagram of a exemplary T2 prepared 3D stack-of-spiral sequence without CSF nulling. The duration of T2 preparation is set as 20, 40, 80, 120, and 160 ms, which changed after acquiring data of a 3D whole brain. The inversion recovery pulse is set as 1100 ms. FIG. 1B illustrates a view of a 3D stack-of-spiral trajectory, with TFE encoding applied on kz dimension and variable density spiral trajectory (Accel=2) applied in plane. FIG. 1C illustrates a schematic diagram of a T2 prepared 3D stack-of-spiral sequence with CSF nulling. The pulse sequence diagram for T2 mapping is shown in FIG. 1A. T2 preparation with 20, 40, 80, 120, 160 ms echo times are successively applied 1.50 s after the WET pre-saturation pulse to generate different T2 contrast. A 3D stack-of-spiral turbo-field-echo (TFE) acquisition was adopted, in which TFE encoding was applied along a kz dimension, as illustrated in FIG. 1B. The interleaves are rotated after every four shot-intervals. For the purpose of CSF nulling, a T2 prep (300 ms) module and inversion pulse (1100 ms) is implemented, as illustrated in FIG. 1C. This T2 prep module and inversion pulse saturates tissues with relatively short T2 values and thus renders higher longitudinal magnetization after recovery.

In an exemplary implementation of the present invention, which is included merely by way of example, and is not meant to be considered limiting, in vivo brain data were acquired on four healthy volunteers (3 females, age 44-59 yo). Three experiments were performed on each volunteer, which consisted of (1) fully sampled equal-spaced spiral trajectory without CSF nulling, used as the reference of T2 estimation; (2) variable density spiral acquisition (Accel=2) without CSF nulling, and (3) variable density spiral acquisition (Accel=2) with CSF nulling. Each dataset was acquired with 1.2 mm isotropic resolution, FOV=220×220× 80 mm$^3$, TFE factor=25. The total acquisition time was 11:00, 5:35 and 8:05 minutes separately.

The k-space dataset with variable density trajectory was retrospectively undersampled by selecting different interleaves to simulate an interleave-rotated and an interleave-no-rotated undersampled acquisition along parametric dimension with in-plane acceleration factor of 5.

For T2 estimation, a model-based iterative reconstruction method with spatial sparsity regularization was applied, which can be formulated as:

$$\text{minimize} \|S(\tilde{f}) - \tilde{f}\|_1 + \alpha TV(\tilde{f})$$

$$s.t. \|E(\tilde{f}) - y\|_2 < \varepsilon$$

where $\tilde{f}$ is the parametric image series, S is the T2 decay model, $\tilde{S}$ is the inverse operator mapping from image series to T2 map, E is the encoding matrix, TV is the total variation transformation, and y is the measured k-space data. Parameter a trades sparsity with model consistency, and E is chosen by the noise level. The algorithm was implemented using projected-gradient approach, which is similar to PG-MOCCO. Data consistency, model consistency and spatial sparsity regularization of images were iteratively optimized.

For comparison purpose, images were reconstructed from the undersampled data of each T2 preparation separately using SENSE and CS SENSE, followed by voxel-wise fit, and also conducted direct T2 estimation using model-based method without spatial sparsity regularization.

FIGS. 2A and 2B illustrate image views of T2 maps and corresponding normalized error maps estimated by different reconstruction methods (SENSE, CS SENSE, model-based method and model-based method with spatial sparsity regularization) and different undersampling schemes along parametric dimension (no-rotated and rotated trajectory) with an in-plane acceleration factor of 5. A reference value of the T2 map was calculated based on the fully sampled data and voxel-wise fit.

FIGS. 2A and 2B compare the T2 maps estimated by different reconstruction methods, which demonstrates that the proposed method of the present invention provided lower noise level and better artifact reduction. The normalized root mean square error (nRMSE) measuring over 3D whole brain of each volunteer provided in Table 1 further proves that the proposed method yielded the highest accuracy, with nRMSE equal to 8.2±0.5% for acceleration factor of 5.

TABLE 1

The normalized root mean squared error (nRMSE) of the T2 estimation by different reconstruction methods and undersampling schemes to the reference T2 map, measuring over the 3D whole brain of four volunteers with an in-plane acceleration factor of 5.

| nRMSE (%) | SENSE | | CS SENSE | | Model-based | | Model-based + CS | |
| --- | --- | --- | --- | --- | --- | --- | --- | --- |
| | No. Rot. | Rot. | No. Rot. | Rot. | No. Rot. | Rot. | No. Rot. | Rot. |
| volunteer1 | 18.9 | 17.9 | 11.8 | 11.7 | 10.1 | 9.9 | 8.5 | 7.7 |
| volunteer2 | 15.2 | 14.5 | 10.1 | 9.8 | 9.6 | 9.2 | 8.4 | 8.0 |
| volunteer3 | 14.9 | 14.7 | 11.1 | 11.1 | 10.0 | 9.9 | 8.9 | 8.0 |
| volunteer4 | 18.7 | 16.6 | 12.4 | 12.3 | 10.4 | 9.6 | 9.7 | 8.9 |
| mean ± std | 16.9 ± 2.2 | 15.9 ± 1.6 | 11.4 ± 1.0 | 11.2 ± 1.1 | 10.0 ± 0.3 | 9.6 ± 0.3 | 8.9 ± 0.6 | 8.2 ± 0.5 |

Figure 3:
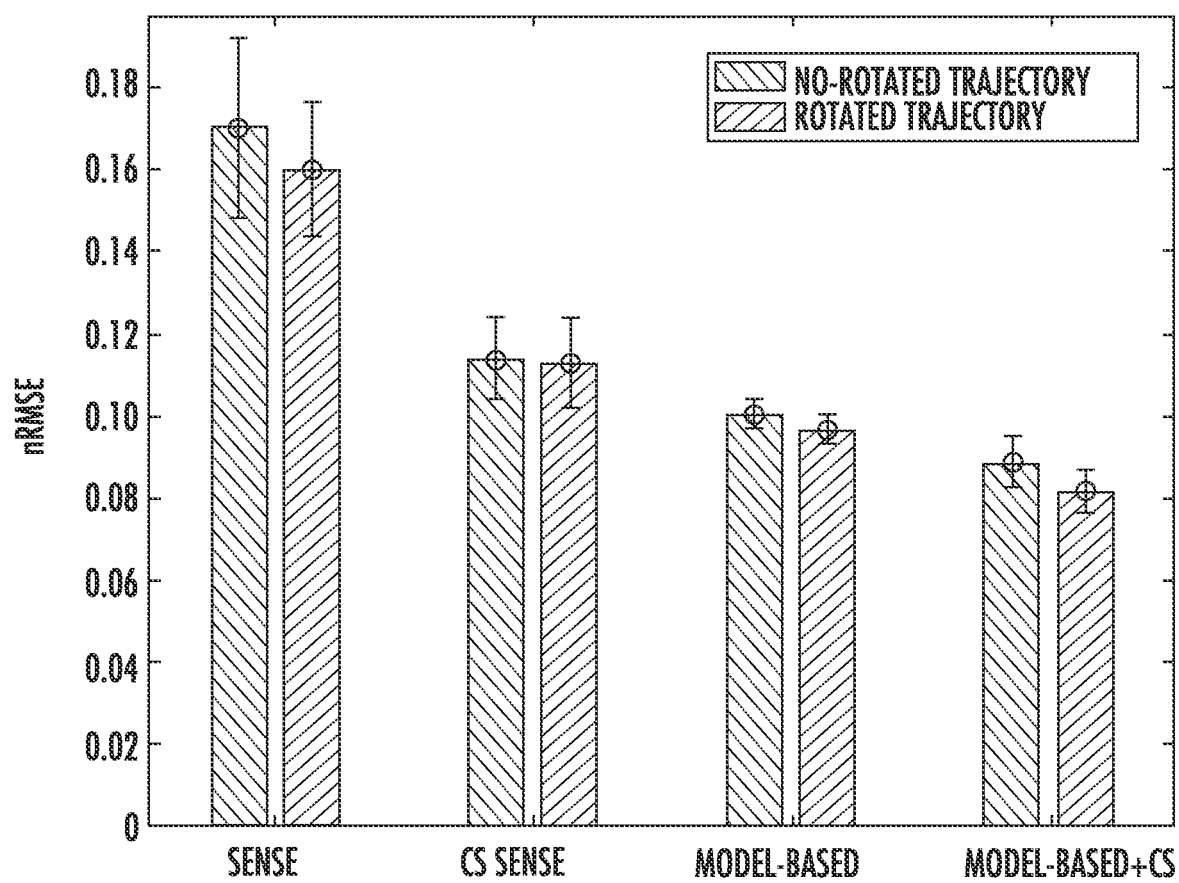
FIG. 3 illustrates a graphical view of a statistical comparison between different reconstruction methods and undersampling schemes in terms of nRMSE of T2 estimation measuring over the 3D whole brain of four volunteers with an in-plane acceleration factor of 5.

FIG. 3 illustrates a graphical view of a statistical comparison between different reconstruction methods and undersampling schemes in terms of nRMSE of T2 estimation measuring over the 3D whole brain of four volunteers with an in-plane acceleration factor of 5. FIG. 3 demonstrates that the k-space data in parametric dimension provided more information and potential on higher acceleration due to the smaller nRMSE of model-based methods, and that the spatial sparsity constraint further improved the accuracy of T2 estimation. Note that for each reconstruction method, the rotated undersampling scheme achieved better accuracy than the no-rotated one; which was more pronounced and stable in the model-based methods. This observation may be explained by the reason that different undersampling trajectory induces different artifacts which may be compensated and reduced when considering the k-space data along the parametric dimension jointly.

Figure 4:
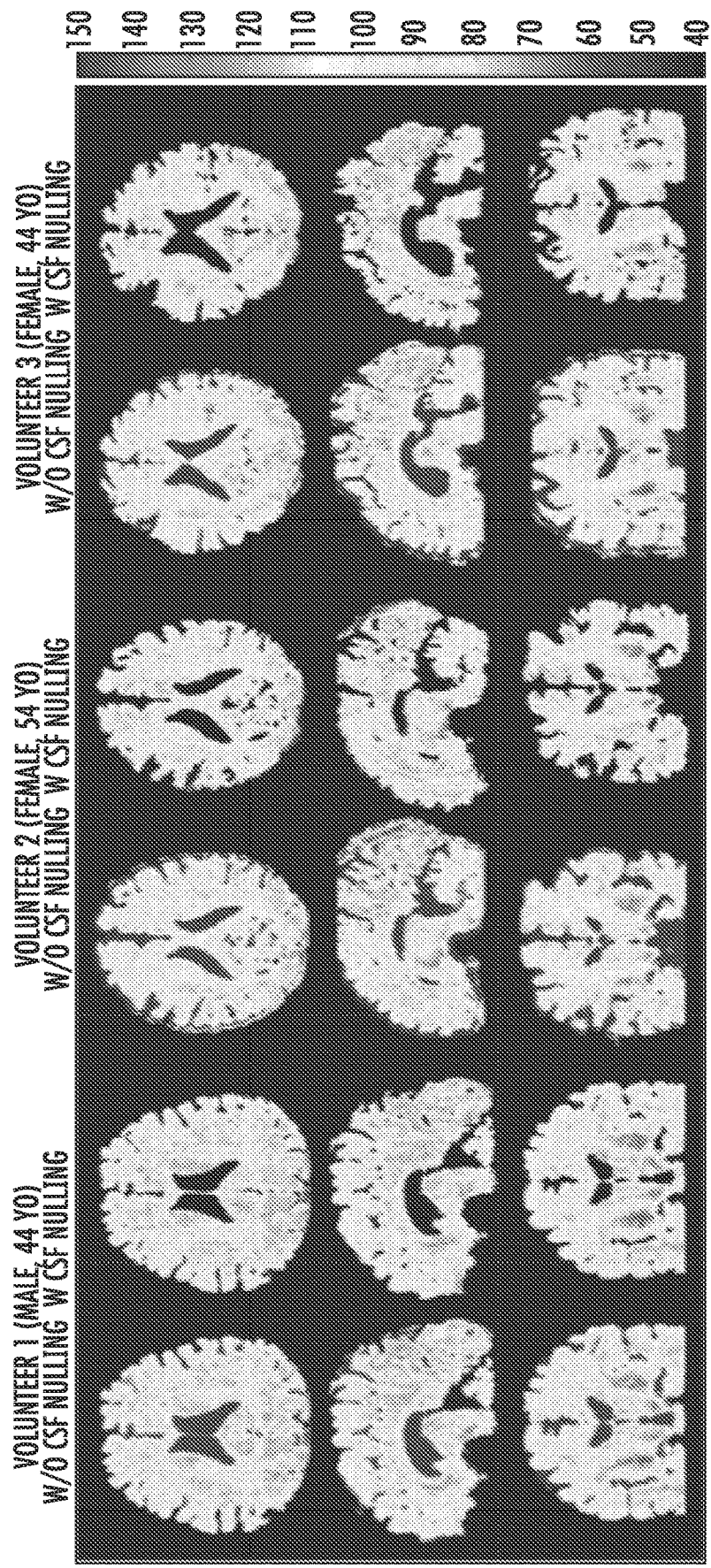
FIG. 4 illustrates an image view of cross-section T2 maps of brains of three healthy volunteers estimated with and without CSF nulling pulse sequences.

FIG. 4 illustrates an image view of cross-section T2 maps of brains of three healthy volunteers estimated with and without CSF nulling pulse sequences. In the CSF nulling results, a mask was created based on the intensities of images with T2 prep duration equal to 20 ms, in which CSF have much lower intensity than other tissue. The nRMSE of T2 estimation with CSF nulling was 8.2±0.8%, which was in agreement with the performance without CSF nulling.

A T2 prepared stack-of-spiral GRE pulse sequence with or without CSF nulling for 3D T2 mapping with whole-brain coverage is described herein. The iterative reconstruction method, which utilized the model consistency, data consistency and spatial sparsity jointly, provided reasonable T2 estimation with an acceleration factor of 5. It should be noted that a similar structure is used for a T1 sequence and reconstruction. The T1 and T2 sequences can be used together or separately.

It should be noted that the pulse sequences, imaging protocols, described herein can be executed with a program(s) fixed on one or more non-transitory computer readable medium. The non-transitory computer readable medium can be loaded onto a computing device, server, imaging device processor, smartphone, tablet, phablet, or any other suitable device known to or conceivable by one of skill in the art.

It should also be noted that herein the steps of the method described can be carried out using a computer, non-transitory computer readable medium, or alternately a computing device, microprocessor, or other computer type device independent of or incorporated with an imaging or signal collection device. An independent computing device can be networked together with the imaging device either with wires or wirelessly. The computing device for executing the present invention can be a completely unique computer designed especially for the implementation of this method.

Indeed, any suitable method of analysis known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape.

It should be noted that the software associated with the present invention is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for magnetic resonance image or spectrum acquisition of a subject, comprising:
    nulling a fluid signal with an inversion model, wherein the inversion model comprises applying an inversion recovery pulse with a magnetic resonance imager;
    minimizing a partial volume effect with the application of the inversion model.

2. The method of claim 1 further comprising applying the inversion module to a T1 pulse sequence.

3. The method of claim 1 further comprising applying the inversion module to a T2 pulse sequence.

4. The method of claim 1 further comprising applying the inversion module to a diffusion pulse sequence.

5. The method of claim 1 further comprising applying a pulse sequence for 3D mapping.

6. A method for obtaining a magnetic resonance image or spectrum of a subject, comprising:
    applying a prepared stack-of-spiral gradient-echo (GRE) pulse sequence for 3D mapping using a magnetic resonance imager;
    applying a model-based reconstruction method with spatial sparsity regularization for mapping using the magnetic resonance imager; and
    nulling a fluid signal with an inversion model, wherein the inversion model comprises applying an inversion recovery pulse with the magnetic resonance imager;
    minimizing a partial volume effect with the application of the inversion model.

7. The method of claim 6 further comprising applying the prepared stack-of-spiral gradient-echo pulse sequence with CSF nulling.

8. The method of claim 6 further comprising applying the prepared stack-of-spiral gradient-echo pulse sequence without CSF nulling.

9. The method of claim 6 further comprising applying a T1 prepared stack-of-spiral gradient-echo (GRE) pulse sequence for 3D T1 mapping.

10. The method of claim 6 further comprising applying a T2 prepared stack-of-spiral gradient-echo (GRE) pulse sequence for 3D T2 mapping.

11. The method of claim 6 further comprising applying a T1 and T2 prepared stack-of-spiral gradient-echo (GRE) pulse sequences for 3D T1 and T2 mapping.

12. The method of claim 6 further comprising applying a diffusion prepared stack-of-spiral gradient-echo (GRE) pulse sequence for 3D diffusion mapping.

* * * * *